(12) United States Patent
Schiell et al.

(10) Patent No.: US 6,956,061 B2
(45) Date of Patent: Oct. 18, 2005

(54) POLYISOPRENYLBENZOPHENONE DERIVATIVES, PROCESSES FOR THEIR PREPARATION AND USE THEREOF

(75) Inventors: Matthias Schiell, Brechen (DE); Michael Kurz, Hofheim (DE); Sabine Haag-Richter, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 116 days.

(21) Appl. No.: 10/632,064

(22) Filed: Jul. 31, 2003

(65) Prior Publication Data

US 2004/0082662 A1 Apr. 29, 2004

Related U.S. Application Data

(60) Provisional application No. 60/438,284, filed on Jan. 6, 2003.

(30) Foreign Application Priority Data

Aug. 7, 2002 (DE) .......................................... 102 36 262

(51) Int. Cl.$^7$ ...................... A61K 31/12; C07C 49/115; A61P 31/00
(52) U.S. Cl. ...................... 514/681; 514/678; 568/327; 568/308
(58) Field of Search ............................. 568/327, 308; 514/681, 678

(56) References Cited

FOREIGN PATENT DOCUMENTS

WO       WO 03/043966 A2       5/2003

OTHER PUBLICATIONS

A. V. Rama Rao et al., Camboginol and Cambogin, Tetrahedron Letters, (1980, pp. 1795–1978, vol. 21).

John Lokvam et al., Two Polyisoprenylated Benzophenones from the trunk latex of *Clusia grandiflora* (Clusiaceae), Phytochemistry, (2000, pp. 29–34, vol. 55).

Richard W. Fuller et al., Guttiferone F, the First Prenylated Benzophenone from *Allanblackia Stuhlmannii*, J. Nat. Prod. (1999, pp. 130–132, vol. 62).

*Primary Examiner*—Taofiq Solola
*Assistant Examiner*—Robert Shiao
(74) *Attorney, Agent, or Firm*—Joseph Strupczewski

(57) ABSTRACT

The present invention relates to compounds of the formula (I):

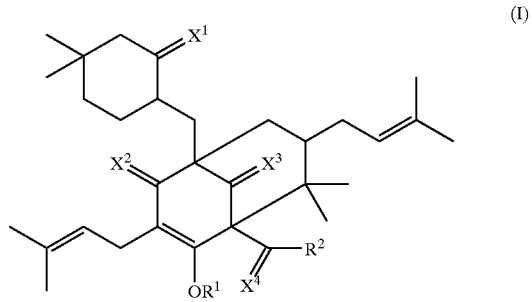

which are produced by the plant *Garcinia punctata*, chemical derivatives derived therefrom, a process for their preparation, and their use as pharmaceuticals, in particular for the treatment and/or prophylaxis of bacterial infectious diseases.

9 Claims, No Drawings

POLYISOPRENYLBENZOPHENONE DERIVATIVES, PROCESSES FOR THEIR PREPARATION AND USE THEREOF

This application claims the benefit of U.S. Provisional Application No. 60/438,284 filed Jan. 6, 2003, and the right of priority from German Patent Application No. 10236262.9, filed Aug. 7, 2002.

A large number of antibiotics are employed for the treatment of bacterial infectious diseases. The causative organisms, however, are becoming increasingly resistant to the pharmaceuticals used, and a great danger threatens due to "multiresistant" microorganisms, which have not only become resistant to individual groups of antibiotics, such as, for example, β-lactam antibiotics, glycopeptides or macrolides, but at the same time carry multiresistances. There are even causative organisms which have become resistant to all commercially obtainable antibiotics. Infectious diseases which are caused by such microorganisms are no longer treatable. There is therefore a great need for new agents which can be employed against resistant microorganisms. There are admittedly many thousands of antibiotically active compounds which have been described in the literature, which are mainly, however, too toxic in order to be able to be employed as pharmaceuticals.

A number of substances of the polyisoprenylbenzophenone type have already been described. These are mainly substances isolated from plants. For instance, Rama Rao et al. (Tetrahedron Lett., 1980, 21, 1975–1978) describe camboginol and cambogin, which can be isolated from *Garcinia gambogia*, and for which no pharmacological action has been described. Fuller et al. (J. Nat. Prod., 1999, 62, 130–132) describe the compound guttiferone F, which has an HIV-inhibitory action. Lokvam et al. (Phytochemistry, 2000, 55, 29–34) describe the compounds chamone I and nemorosome II as active against certain bee-pathogenic bacteria.

It is the object of the present invention to make available alternative compounds of the polyisoprenylbenzophenone type having improved pharmacological actions. It has surprisingly been found that the plant *Garcinia punctata* from the Clusiaceae family is able to form novel compounds which are active, in particular, against human-pathogenic bacteria.

The invention therefore relates to a compound of the formula (I):

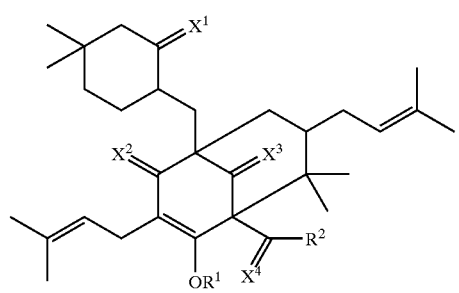

(I)

wherein:

$R^1$ is H, $C_1$–$C_6$-alkyl, $C_2$–$C_6$-alkenyl, $C_2$–$C_6$-alkynyl or $C_6$–$C_{14}$-aryl, in which alkyl, alkenyl, alkynyl and aryl are unsubstituted or mono- to trisubstituted by a radical $R^3$, $R^2$ is $C_1$–$C_6$-alkyl, $C_2$–$C_6$-alkenyl, $C_2$–$C_6$-alkynyl or $C_6$–$C_{14}$-aryl, in which alkyl, alkenyl, alkynyl and aryl are unsubstituted or substituted n times by a radical $R^3$, where n is an integer from 1 to 3, and $R^3$ is —OH, =O, —O—$C_1$–$C_6$-alkyl, —O—$C_2$–$C_6$-alkenyl, —O—$C_6$–$C_{14}$-aryl, —NH—$C_1$–$C_6$-alkyl, —NH—$C_2$–$C_6$-alkenyl, —NH[—C(=O)—($C_1$–$C_6$-alkyl)], —NH[—C(=O)—($C_6$–$C_{14}$-aryl)], —$NH_2$ or halogen, when $R^1$ and $R^2$ are each independently alkyl, alkenyl and alkynyl, and when $R^1$ and $R^2$ are each independently aryl, $R^3$ is —OH, —O—$C_1$–$C_6$-alkyl, —O—$C_2$–$C_6$-alkenyl, —O—$C_6$–$C_{14}$-aryl, —NH—$C_1$–$C_6$-alkyl, —NH—$C_2$–$C_6$-alkenyl, —NH[—C(=O)—($C_1$–$C_6$-alkyl)], —NH[—C(=O)—($C_6$–$C_{14}$-aryl)], —$NH_2$ or halogen, in which alkyl and alkenyl can be further substituted by —CN, -amide or -oxime functions, and aryl can be further substituted by —CN or -amide functions, $X^1$ is $CH_2$ or O, $X^2$, $X^3$ and $X^4$ independently of one another are O, $NR^1$ or S, or a stereoisomeric form of the compound of the formula (I) or a mixture of stereoisomers of a compound of the formula (I) in any ratio, or a physiologically tolerable salt of a compound of the formula (I) or a physiologically tolerable salt of a stereoisomeric form of a compound of the formula (I).

As used herein, "$C_1$–$C_6$-alkyl" is a straight-chain or branched alkyl having 1 to 6 C atoms, preferably having 1 to 4 C atoms, e.g. methyl, ethyl, i-propyl, tert-butyl and hexyl.

As used herein, "$C_2$–$C_6$-alkenyl" is a straight-chain or branched alkenyl having 2 to 6 C atoms, which is mono-, di- or triunsaturated, e.g. allyl, crotyl, 1-propenyl, penta-1,3-dienyl and pentenyl.

As used herein, "$C_2$–$C_6$-alkynyl" is a straight-chain or branched alkynyl having 2 to 6 C atoms, which is mono- or diunsaturated, e.g. propynyl, butynyl and pentynyl.

As used herein, "$C_6$–$C_{14}$-aryl" is an aromatic radical having 6 to 14 C atoms, preferably 6 to 10 C atoms, for example phenyl, 1-naphthyl or 2-naphthyl, which is unsubstituted or substituted by halogen, $C_1$–$C_4$-alkyl, preferably methyl, hydroxyl, $C_1$–$C_4$-alkoxy, preferably methoxy, or by trifluoromethyl.

As used herein, "aliphatic N-acyl groups —NH[—C(=O)—($C_1$–$C_6$-alkyl)]" preferably contain a $C_1$–$C_4$-alkyl group, for example formyl, acetyl, propionyl, butyryl, hexanoyl, acryloyl, crotonoyl, propioloyl, and can be further substituted by halogen, preferably chlorine, bromine, fluorine, by $NH_2$, and/or by —NH($C_1$–$C_6$-alkyl), preferably —NH($C_1$–$C_4$-alkyl), for example methyl- or ethylamino. "Aromatic N-acyl groups —NH[—C(=O)—($C_6$–$C_{14}$-aryl)]" are, for example, N-benzoyl or N-naphthoyl, and can be further substituted by halogen, preferably chlorine, bromine, fluorine, by $C_1$–$C_6$-alkyl, preferably $C_1$–$C_4$-alkyl, for example methyl, by hydroxy, by —NH($C_1$–$C_6$-alkyl), preferably —NH($C_1$–$C_4$-alkyl), for example methyl- or ethylamino, or —O—$C_1$–$C_6$-alkyl, preferably —O—$C_1$–$C_4$-alkyl, for example methoxy.

As used herein, "halogen" is an element of the 7th main group of the periodic table, preferably chlorine, bromine, fluorine.

As used herein, "treat" or "treating" means any treatment, including but not limited to, alleviating symptoms, eliminating the causation of the symptoms either on a temporary or permanent basis, or to preventing or slowing the appearance of symptoms and progression of the named disease, disorder or condition.

As used herein, "prophylaxis" refers to the prevention of disease.

For the compound of formula (I):
$R^1$ is preferably H.
$R^2$ is preferably $C_6$–$C_{14}$-aryl, particularly preferably $C_6$–$C_{10}$-aryl, especially preferably phenyl, unsubstituted or substituted by $(R^3)_n$. Particularly preferably, $R^2$ is phenyl or a 3,4-dihydroxyphenyl radical.
$R^3$ is preferably OH.
n is preferably 1 or 2.
$X^1$ is preferably $CH_2$.
$X^2$, $X^3$ and $X^4$ are preferably O.

The general definitions of the radicals and the preferred definitions of the radicals $R^1$, $R^2$, $R^3$, $X^1$, $X^2$, $X^3$, $X^4$ and n can be combined with one another independently of one another in any desired manner.

Tautomeric forms of the compound (I) may exist and are, for example, compounds of the formula (I-A):

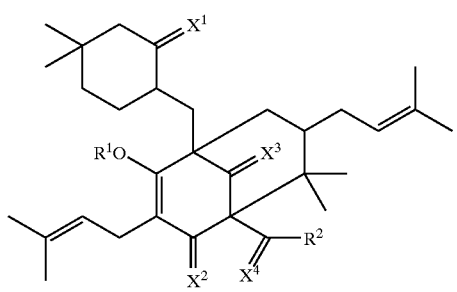

(I-A)

where the radicals $R^1$, $R^2$, $X^1$, $X^2$, $X^3$ and $X^4$ are as defined above.

The invention preferably relates to a compound of the formula (II):

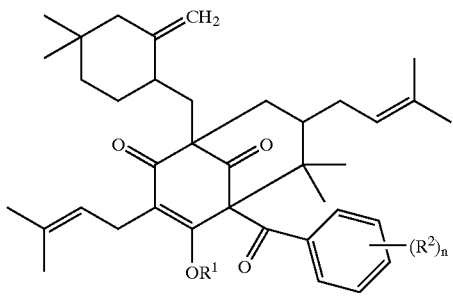

(II)

where $R^1$, $R^2$ and n have the abovementioned meanings.

Particularly preferred, is a compound of the formula (III), which is also described as makandechamone below:

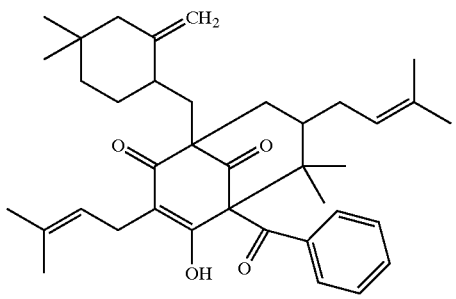

(III)

As used herein, stereoisomeric form means enantiomer, diastereomer and/or tautomer. Chiral centers in the compounds of the formulae (I), (I-A), (II) and (III) can be present in the R or in the S configuration. The invention relates both to the optically pure compounds and to mixtures of stereoisomers, such as mixtures of enantiomers and mixtures of diastereomers, in any ratio.

The compounds according to the invention differ from substances known from the literature, for example, by their polarity, their chemical structure or their antimicrobial activity or further physical properties.

The invention furthermore relates to obvious chemical equivalents of the compounds of the formula (I), (II) or (III). Obvious chemical equivalents of the compounds according to the invention are compounds which have the same activity as the compounds according to the invention and exhibit a slight chemical difference or are converted into the compounds according to the invention under mild conditions. The equivalents mentioned include, for example, esters, azomethines (Schiff's bases), ketals, oximes, hydrogenation products, reduction products, complexes or adducts of the or with the compounds according to the invention.

The invention additionally relates to makandechamone, a compound of the empirical formula $C_{38}H_{50}O_4$, detected by ESI spectroscopy, and characterized by the $^1$H-NMR and $^{13}$C-NMR data according to table 2 (see below), or a stereoisomeric form of the compound makandechamone or a mixture of the respective aforementioned forms in any ratio, or a physiologically tolerable salt of the compound makandechamone or a stereoisomeric form of the compound makandechamone.

The invention further relates to a compound of the empirical formula $C_{38}H_{50}O_4$ (makandechamone) obtainable by extraction of leaves of the plant Garcinia punctata or a variant and/or mutant of Garcinia punctata and subsequent isolation, and optionally conversion into a pharmacologically tolerable salt.

The invention furthermore relates to a process for the preparation of the compound of the formula (I) or of a pharmacologically tolerable salt of the compound of the formula (I), which comprises
(a) extracting parts of the plant Garcinia punctata or a variant and/or mutant of Garcinia punctata,
(b) isolating and optionally purifying a compound of the formula (III),
(c) derivatizing the compound of the formula (III), if appropriate, to give a compound of the formula (I), and
(d) converting the compound of the formula (I), if appropriate, into a pharmacologically tolerable salt.

The invention furthermore relates to a process for the preparation of the compound of the formula (III) or of a pharmacologically tolerable salt of the compound of the formula (III), which comprises
(a) extracting parts of the plant Garcinia punctata or a variant and/or mutant of Garcinia punctata,
(b) isolating and optionally purifying a compound of the formula (III),
(c) converting the compound of the formula (III), if appropriate, into a pharmacologically tolerable salt.

Preferably, makandechamone of the formula (III) can be esterified and/or mono- or polyhydrogenated by methods well known in the art. In esterifications, the hydroxy group of makandechamone, which is part of a vinylogous ester, is esterified, for example, using an alkylating agent, such as, for example, diazomethane or trimethylsilyldiazomethane. Hydrogenations of one or more double bonds and/or carbonyl groups of the compound of the formula (III) can be reduced using a reductant, double bonds, for example, being reduced using $H_2$/Pd and carbonyl groups, for example, using NaBH$_4$. The abovementioned methods for derivatization are described in textbooks such as Jerry March, *Advanced Organic Chemistry*, John Wiley & Sons, 4$^{th}$ Edition, 1992. In order to carry out reactions selectively, it may be advantageous to introduce suitable protective groups before the reaction in a manner known per se. The protective groups can be removed after the reaction.

The extraction of the compounds according to the invention can be monitored according to methods known to the person skilled in the art, such as, for example, by testing the biological activity in bioassays or by chromatographic methods such as thin-layer chromatography (TLC) or high-performance liquid chromatography (HPLC).

*Garcinia punctata* is an evergreen tree of the Clusiaceae family. The range of distribution of the Clusiaceae are the temperate and tropical regions and there are numerous tropical curative and useful plants in this family. The distribution of *Garcinia punctata* is essentially restricted to the West African region; the *Garcinia punctata* plant provided with the number PLA 100848 was collected in Gabon in the immediate vicinity of the La Makandé Research Field Station Station (coordinates 0° 40'860" S-11° 54' 750" E). *Garcinia punctata* has simple opposite leaves and contains orange- to red-colored latex. The flowers are yellow or white. The sample of PLA 100848 from which the compound makandechamone was isolated originates from the area of the treetop.

Screening for mutants and variants which produce the antibiotic according to the invention can be carried out by determination of the biological activity of active compound accumulated in the extracts, for example by determination of the antibacterial action, or by detection of compounds which are known as antibacterially active, in the extracts by, for example, HPLC or LC-MS methods.

Said process comprises the extraction of all parts of the plant *Garcinia punctata*, preferably the leaves. The compound makandechamone occurs, in particular, in the leaves of the plant *Garcinia punctata*, and is preferably obtained from dried leaves. The Clusiaceae family includes numerous curative and useful plants. The plants are widespread in temperate and tropical climates.

The dried and finely ground leaves are extracted with an organic solvent, for example methanol or propan-2-ol, optionally as a mixture with water or an aqueous buffer.

The extraction can be carried out in a wide pH range, but it is expedient to work in a neutral or weakly acidic medium, preferably between pH 3 and pH 7. The extract can be concentrated and dried, for example, in vacuo.

To isolate makandechamone, plants of the same genus can also be used which have been collected at another habitat. The content of makandechamone can of course vary according to habitat conditions, such as, for example, soil condition, temperature, humidity or incidence of light.

The process according to the invention can be employed for extraction and isolation on a laboratory scale (100 g to 1 kg of dry plant matter) and on an industrial scale (100 to >1000 kg).

The plants can be cultivated in open ground or preferably in a greenhouse, alternatively plant cell cultures can be employed for the production of the metabolites. As a rule, to this end cultivation is carried out in a number of stages, i.e. firstly one or more precultures are prepared in a suitable liquid medium, from which the main culture can then be inoculated. The starting material as a rule consists of callus cultures. By means of the choice of suitable bioreactors for culturing the plant cell culture, optimal mixing and aeration of the culture without the action of excessively strong shear forces on the plant cells and thus optimal cell growth and metabolite production can be achieved. For example, airlift or bubble column reactors, and blade or propeller stirrers, can be employed for mixing the cultures. The cells can grow as individual cells or branched or unbranched cell aggregates or chains. Metabolite production can be induced by stimulation with exogenous factors, e.g. heavy metal salts or plant elicitors.

Product formation in the plant cell culture can be monitored by means of the pH of the cultures and by chromatographic methods, such as, for example, thin-layer chromatography, HPLC or testing the biological activity. The compound makandechamone according to the invention can also be contained in other plant parts, in addition to the leaves. The isolation process described below is used for the purification of the compound makandechamone according to the invention.

The isolation or purification of the compounds according to the invention from the plant or the culture medium is carried out according to known methods taking into account the chemical, physical and biological properties of the natural substances. HPLC can be used for the testing of the concentration of the desired compound in the starting material or in the individual isolation steps, the amount of the substance formed expediently being compared using a calibration solution.

For the isolation of makandechamone, the leaves of the plant are harvested and extracted while still in fresh condition or dried, according to the customary processes and then makandechamone is extracted from the plant material using an optionally water-containing organic solvent. The organic solvent phase contains the makandechamone according to the invention, it is optionally concentrated in vacuo and further purified.

A further method of purification is chromatography on adsorption resins such as, for example, on Diaion® HP-20 (Mitsubishi Casei Corp., Tokyo), on Amberlite® XAD 7 (Rohm and Haas, USA), on Amberchrom® CG, (Toso Haas, Philadelphia, USA) or the like. Numerous reversed-phase supports, e.g. RP$_8$ and RP$_{18}$, such as have been generally published, for example, in the context of high-pressure liquid chromatography (HPLC), are moreover suitable.

A further possibility of purification of the compound according to the invention consists in the use of "normal phase chromatographic supports", such as, for example, silica gel or Al$_2$O$_3$ or others, in a manner known per se.

An alternative isolation process is the use of molecular sieves, such as, for example, Fractogel® TSK HW-40 (Merck, Germany) and others, in a manner known per se. It is moreover also possible to obtain makandechamone from enriched material by crystallization. Organic solvents and their mixtures, anhydrous or with the addition of water are, for example, suitable for this. An additional process for the isolation and purification of the antibiotics according to the invention consists in the use of anion exchangers, preferably in the pH range from 4 to 10, and cation exchangers, preferably in the pH range from 2 to 5. Particularly suitable for this purpose is the use of buffer solutions, to which amounts of organic solvents have been added.

The compounds of the formula (I), (II) and (III) can be converted into pharmacologically tolerable salts according to methods known to the person skilled in the art. Pharmacologically tolerable salts of the compounds according to the invention are understood as both inorganic and organic salts, such as are described in Remington's Pharmaceutical Sciences (17th edition, page 1418 [1985]). Possible salts are, in particular, alkali metal, ammonium and alkaline earth metal salts, salts with physiologically tolerable amines and salts with inorganic or organic acids such as, for example, HCl, HBr, $H_2SO_4$, maleic acid and fumaric acid.

It has surprisingly been found that the compounds of the formula (I) according to the invention exhibit antibacterial actions, in particular against human-pathogenic microorganisms, and are therefore suitable for the treatment and/or prophylaxis of diseases which are caused by bacterial infections.

The present invention therefore also relates to the use of one or more of the compounds of the formula (I), (II) and/or (III) according to the invention as pharmaceuticals, in particular for the treatment and/or prophylaxis of bacterial infections.

The invention further relates to the use of one or more of the compounds of the formula (I), (II) and/or (III) according to the invention for the production of pharmaceuticals, in particular for the treatment and/or for the prophylaxis of bacterial infections.

In addition, the present invention relates to a pharmaceutical containing at least one compound of the formula (I), (II) and/or (III). Said pharmaceutical containing a compound of the formula (I), (II) and/or (III) is produced using one or more physiologically suitable excipients and brought into a suitable administration form.

The pharmaceuticals according to the invention can be administered enterally (orally), parenterally (intramuscularly or intravenously), rectally or locally (topically). They can be administered in the form of solutions, powders (tablets, capsules including microcapsules), ointments (creams or gel), or suppositories. Possible physiologically suitable excipients for formulations of this type are the pharmaceutically customary liquid or solid fillers and extenders, solvents, emulsifiers, lubricants, flavor corrigents, colorants and/or buffer substances. As an expedient dose, 0.1–1000, preferably 0.2–100, mg/kg of bodyweight are administered. They are expediently administered in dosage units which contain at least the efficacious daily amount of the compounds according to the invention, e.g. 30–3000, preferably 50–1000, mg.

The following examples should serve to illustrate the invention in greater detail, without restricting the breadth of the invention in any manner whatsoever.

EXAMPLE 1

Preparation of the Crude Extract of the Plant *Garcinia punctata*, PLA-100848

Leaves of *Garcinia punctata*, PLA-100848, were collected in the fresh state and air-dried at a maximum of 40° C. 100 g of dry material were finely ground and extracted with 1 l of methanol for at least 8 h with stirring. The extract was filtered off and then concentrated almost to dryness in vacuo. The residue was resuspended using water and freeze-dried. The primary extract prepared in this way can be stored at 4° C. or −20° C. or used for further isolation as described in example 2. To test the biological activity, tannins and other strongly hydrophilic or lipophilic interfering substances were firstly removed from the primary extract by means of chromatography on polyamide and polystyrene adsorber resin.

EXAMPLE 2

Isolation and Purification of the Compound Makandechamone 1 g of the enriched crude extract of makandechamone, obtained according to example 1, was dissolved in 5 ml of methanol and centrifuged and the supernatant was separated on a LUNA® 10 μm C 18(2)-HPLC column (Phenomenex, USA) (width×height=2.1 cm×25 cm) in a gradient process using 5% to 95% of acetonitrile in 0.1% ammonium acetate pH 4.5. Flow: 33 ml/min. Fraction size: 33 ml. The fractions 44 and 45 investigated by analytical HPLC (see example 4) were collected and freeze-dried. They afforded 15 mg of makandechamone in 95% purity.

EXAMPLE 3

Plant Production, Collection of the Seeds, Sowing and Growth and Production Conditions The seeds of *Garcinia punctata*, PLA 100848, were collected after maturation and sown in a greenhouse for further cultivation of the plants. The optimum temperature was about 28° C. at an atmospheric humidity of 70–90%. The plants were cultivated for a number of months to years, up to harvesting of the leaves or other suitable plant parts.

EXAMPLE 4

Analytical HPLC

| | |
|---|---|
| Column: | Purospher ® STAR RP-18 e 3 μm, 30–2, (Merck, Germany) |
| Mobile phase buffer A: | 5% acetonitrile + 0.1% ammonium acetate, |
| Mobile phase buffer B: | 95% acetonitrile + 0.1% ammonium acetate, |
| Gradient: | 15 min |
| Flow rate: | 0.25 ml per minute |

Detection by UV absorption at 210 nm.

A retention time of 8.9 min was found for makandechamone.

EXAMPLE 5

Characterization of Makandechamone

The physicochemical and spectroscopic properties of the antibiotic according to the invention can be summarized as follows:

Appearance:

Colorless to pale yellow substance, soluble in medium polar and polar organic solvents, not very soluble in water. Stable in neutral and acidic medium.

| | |
|---|---|
| Empirical formula: | $C_{38}H_{50}O_4$ |
| Molecular weight: | 570.82 |
| $^1$H- and $^{13}$C-NMR: | see table 1 |
| UV maxima: | 240 nm, 290 nm |

Determination of the Molecular Peak:

The molecule sought is assigned the mass 570 on the basis of the following results: ESI$^+$ spectrum shows a peak at 571 amu (M+H)$^+$, MS/MS ESI$^+$: 447 amu (M+H)$^+$, 435 amu, 379 amu, 311 amu, 255 amu, 177 amu, 105 amu High resolution of the quasi-molecular ion: ESI$^+$ 571.3783 (M+H)$^+$, 571.3782 was calculated for the empirical formula $C_{38}H_{50}O_4$.

TABLE 1

$^1$H- and $^{13}$C-NMR chemical shifts of makandechamone in MeOD at 303 K.

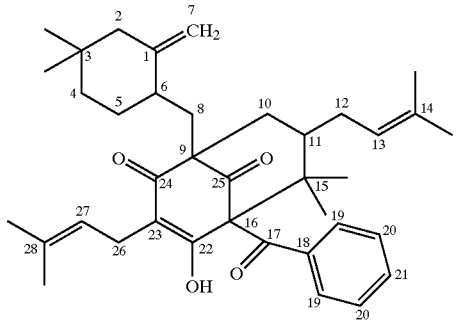

| | $^1$H | $^{13}$C |
|---|---|---|
| 1 | — | 151.79 |
| 2 | 2.04/1.66 | 49.0 |
| 3 | — | 33.52 |
| 3-Me | 0.84 | 29.20 |
| 3-Me' | 0.83 | 28.31 |
| 4 | 1.49/1.17 | 38.59 |
| 5 | 1.55/1.31 | 31.18 |
| 6 | 2.37 | 40.04 |
| 7 | 4.62/4.53 | 108.31 |
| 8 | 2.10/1.98 | 34.59 |
| 9 | — | ~61.5[a] |
| 10 | 2.00/1.42 | 45.06 |
| 11 | 1.70 | 44.11 |
| 12 | 2.11/1.71 | 28.31 |
| 13 | 4.99 | 124.00 |
| 14 | — | 134.17 |
| 14-Me | 1.68 | 25.98 |
| 14-Me' | 1.58 | 17.97 |
| 15 | — | ~49.0 |
| 15-Me | 1.34 | 24.56 |
| 15-Me' | 1.10 | 16.23 |
| 16 | — | ~77.6[a] |
| 17 | — | 195.20 |
| 18 | — | 138.70 |
| 19 | 7.64 | 129.63 |
| 20 | 7.28 | 128.83 |
| 21 | 7.46 | 133.05 |
| 22 | — | [b] |
| 23 | — | 120.30 |
| 24 | — | [b] |
| 25 | — | 209.88 |
| 26 | 3.20/3.07 | 22.42 |
| 27 | 5.09 | 121.95 |
| 28 | — | 133.46 |
| 28-Me | 1.68 | 18.15 |
| 28-Me' | 1.66 | 26.09 |

[a] No signal is observed in the $^{13}$C spectrum for this C atom. Assignment was carried out by means of correlations in the HMBC spectrum.
[b] No signal is observed in the $^{13}$C spectrum for this C atom.

EXAMPLE 6

Test of the Antibacterial Activity

For the test of the antibacterial action, agar plates containing 2 ml of *Staphylococcus aureus* sowing in 200 ml of agar solution were firstly prepared. Makandechamone was applied in a 1 mg/ml solution to antibiotic test sheets (Schleicher and Schüll) having a diameter of 6 mm and placed on the agar plate. The inoculated *Staphylococcus* plates were incubated for 16 hours at 37° C. Inhibition halos having the following diameters (mm) were then observed:

| Amount | Inhibition halo size (mm) |
|---|---|
| 10 µl | 7 |
| 20 µl | 12 |
| 40 µl | 14. |

What is claimed is:

1. A compound of the formula (I):

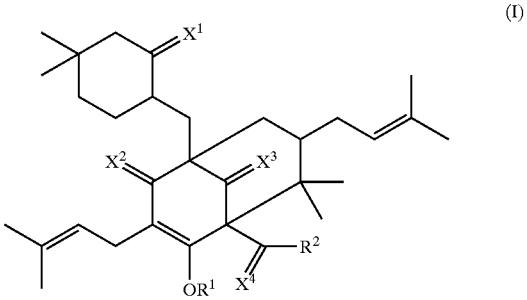

wherein:

R$^1$ is H, C$_1$–C$_6$-alkyl, C$_2$–C$_6$-alkenyl, C$_2$–C$_6$-alkynyl, or C$_6$–C$_{14}$-aryl, in which alkyl, alkenyl, alkynyl and aryl are unsubstituted or mono- to tri-substituted by a radical R$^3$, R$^2$ is C$_1$–C$_6$-alkyl, C$_2$–C$_6$-alkenyl, C$_2$–C$_6$-alkynyl, or C$_6$–C$_{14}$-aryl, in which alkyl, alkenyl, alkynyl and aryl are unsubstituted or substituted n times by a radical R$^3$, where n is an integer from 1 to 3, and R$^3$ is —OH, =O, —O—C$_1$–C$_6$-alkyl, —O—C$_2$–C$_6$-alkenyl, —O—C$_6$–C$_{14}$-aryl, —NH—C$_1$–C$_6$-alkyl, —NH—C$_2$–C$_6$-alkenyl, —NH[—C(=O)—(C$_1$–C$_6$-alkyl)], —NH[—C(=O)—(C$_6$–C$_{14}$-aryl)], —NH$_2$ or halogen, when R$^1$ and R$^2$ are each independently alkyl, alkenyl and alkynyl, and when R$^1$ and R$^2$ are each independently aryl, R$^3$ is —OH, —O—C$_1$–C$_6$-alkyl, —O—C$_2$–C$_6$-alkenyl, —O—C$_6$–C$_{14}$-aryl, —NH—C$_1$–C$_6$-alkyl, —NH—C$_2$–C$_6$-alkenyl, —NH[—C(=O)—(C$_1$–C$_6$-alkyl)], —NH[—C(=O)—(C$_6$–C$_{14}$-aryl)], —NH$_2$ or halogen, in which alkyl and alkenyl can be further substituted by —CN, -amide or -oxime, and aryl can be further substituted by —CN or -amide, X$^1$ is CH$_2$ or O, X$^2$, X$^3$ and X$^4$ independently of one another are O, NR$^1$ or S, wherein R$^1$ is as previously defined, or a stereoisomeric form of the compound of the formula (I) or a mixture of stereoisomers of a compound of the formula (I) in any ratio, or a physiologically tolerable salt of a compound of the formula (I) or a physiologically tolerable salt of a stereoisomeric form of a compound of the formula (I).

2. The compound according to claim 1 which is the compound of formula (II):

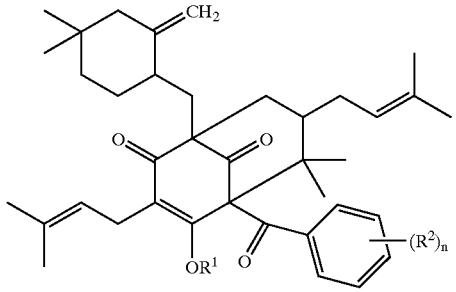

wherein $R^1$ $R^2$ and n are as previously defined.

3. The compound according to claim 2, which is the compound of formula (III):

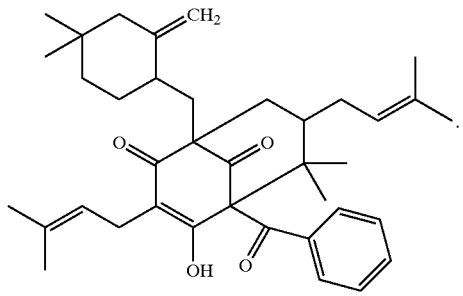

4. A process for the preparation of a compound of the formula (I) according to claim 1 comprising:

(a) extracting parts of the plant *Garcinia punctata* or one of its variants and/or mutants, (b) isolating and optionally purifying a compound of the formula (III):

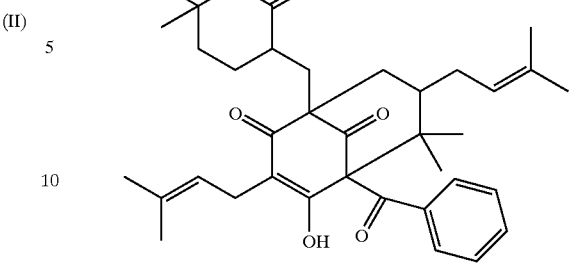

(c) derivatizing the compound of the formula (III), if appropriate using a suitable reagent, to give a compound of the formula (I) and, (d) converting the compound of the formula (I), if appropriate, into a pharmacologically tolerable salt.

5. The process according to claim 4 for the preparation of a compound of the formula (III) comprising:

(a) extracting parts of the plant *Garcinia punctata* or one of its variants and/or mutants, (b) isolating and optionally purifying a compound of the formula (III), and (c) converting the compound of the formula (III), if appropriate, into a pharmacologically tolerable salt.

6. A compound as claimed in claim 1 for the use as a pharmaceutical.

7. A method for the treatment or prophylaxis of bacterial infections comprising administering to a patient in need of said treatment an effective amount of a compound according to claim 1 or a pharmacologically tolerable salt thereof.

8. A pharmaceutical composition comprising a compound of claim 1 or a pharmacologically tolerable salt thereof and one or more physiologically acceptable excipients.

9. A process for the production of a pharmaceutical composition as claimed in claim 8, comprising bringing a compound of the formula I, or a pharmacologically tolerable salt thereof, into a suitable administration form using one or more physiologically suitable excipients.

* * * * *